(12) United States Patent
Hunter

(10) Patent No.: US 6,697,517 B1
(45) Date of Patent: Feb. 24, 2004

(54) PARTICLE DETECTION AND EMBEDDED VISION SYSTEM TO ENHANCE SUBSTRATE YIELD AND THROUGHPUT

(75) Inventor: Reginald Hunter, Round Rock, TX (US)

(73) Assignee: Applied Magerials, Inc., Santa Clara, CA (US)

(*) Notice: Subject to any disclaimer, the term of this patent is extended or adjusted under 35 U.S.C. 154(b) by 0 days.

(21) Appl. No.: 09/546,644

(22) Filed: Apr. 10, 2000

Related U.S. Application Data

(63) Continuation of application No. 09/391,341, filed on Sep. 7, 1999.

(51) Int. Cl.$^7$ .................................................. G06K 9/00
(52) U.S. Cl. ................................... 382/149; 356/237.5
(58) Field of Search ................................ 382/141, 145, 382/147, 148, 149, 181; 348/87, 126; 356/237.3, 237.4, 237.5; 250/559.04, 559.41, 559.42, 559.43, 559.46, 559.45, 559.05, 559.06, 559.08, 559.39, 559.4; 438/16

(56) References Cited

U.S. PATENT DOCUMENTS

| | | | |
|---|---|---|---|
| 4,441,124 A | 4/1984 | Heebner et al. | 348/126 |
| 4,449,818 A | 5/1984 | Yamaguchi et al. | 356/237.3 |
| 4,499,595 A | 2/1985 | Masaitis et al. | 382/177 |
| 4,626,101 A | 12/1986 | Ogawa et al. | 356/237 |
| 4,772,126 A | 9/1988 | Allemand et al. | 356/336 |
| 4,893,932 A | 1/1990 | Knollenberg | 356/369 |
| 4,898,471 A | 2/1990 | Vaught et al. | 356/394 |
| 4,920,385 A | 4/1990 | Clarke et al. | 356/237 |
| 4,941,980 A | 7/1990 | Halavee et al. | 250/310 |
| 4,969,748 A | 11/1990 | Crowley et al. | 374/1 |
| 4,989,973 A | 2/1991 | Noso et al. | 356/239 |
| 5,058,178 A | 10/1991 | Ray | 382/150 |
| 5,120,034 A | 6/1992 | Van Engelen et al. | 269/73 |

(List continued on next page.)

FOREIGN PATENT DOCUMENTS

| | | | |
|---|---|---|---|
| EP | 0 206 709 A2 | 12/1986 | G06K/9/00 |
| EP | 0 398 781 A3 | 11/1990 | G01N/21/88 |
| EP | 0 638 801 A | 2/1995 | G01N/21/88 |
| EP | 0 821 085 A1 | 1/1998 | C30B/31/10 |

(List continued on next page.)

OTHER PUBLICATIONS

Written Opinion (Form PCT/IPEA/408), dated Jan. 10, 2003 for PCT/US01/42470.
Written Opinion for PCT/US01/31293, dated Dec. 31, 2002.
International Search Report for PCT/US01/31079, dated Jun. 24, 2002.

(List continued on next page.)

*Primary Examiner*—Samir Ahmed
(74) *Attorney, Agent, or Firm*—Moser Patterson & Sheridan

(57) ABSTRACT

The present invention generally provides an apparatus and a method for scanning a substrate in a processing system. A transmitter unit and a receiver unit are disposed on a processing system and cooperate to transmit and detect energy, respectively. The transmitter unit is positioned to transmit a signal onto the substrate surface moving between vacuum chambers, one of which is preferably a transfer chamber of a cluster tool. Features disposed on the substrate surface, which may include particles, devices, alphanumeric characters, the substrate edges, notches, etc., cause a scattering or reflection of a portion of the signal. The receiver unit is disposed to collect the scattered/reflected portion of the signal and direct the same to a processing unit. Preferably, the transmitter unit comprises a laser source and the receiver unit comprises a charged-coupled device (CCD). Preferably, the invention is integrally positioned in a processing system to allow substrate inspection during normal operation and provide real-time information.

23 Claims, 8 Drawing Sheets

U.S. PATENT DOCUMENTS

| | | | |
|---|---|---|---|
| 5,177,559 A | 1/1993 | Batchelder et al. | 356/237.5 |
| 5,186,718 A | 2/1993 | Tepman et al. | 29/25.01 |
| 5,233,191 A | 8/1993 | Noguchi et al. | 250/306 |
| 5,274,434 A | 12/1993 | Morioka et al. | 356/237 |
| 5,416,594 A | 5/1995 | Gross et al. | 356/237 |
| 5,463,459 A | 10/1995 | Morioka et al. | 356/237 |
| 5,465,152 A | 11/1995 | Bilodeau et al. | 356/371 |
| 5,479,252 A | 12/1995 | Worster et al. | 356/237 |
| 5,483,138 A | 1/1996 | Shmookler et al. | 318/568.16 |
| 5,486,919 A | 1/1996 | Tsuji et al. | 356/349 |
| 5,563,798 A | 10/1996 | Berken et al. | 700/218 |
| 5,637,881 A | 6/1997 | Burghard et al. | 250/573 |
| 5,644,393 A | 7/1997 | Nakamura et al. | 356/237 |
| 5,646,725 A | 7/1997 | Hagiwara | 356/237 |
| 5,659,172 A | 8/1997 | Wagner et al. | 250/307 |
| 5,663,569 A | 9/1997 | Hayano | 250/559.45 |
| 5,694,214 A | 12/1997 | Watanabe et al. | 356/237 |
| 5,699,447 A | 12/1997 | Alumot et al. | 382/145 |
| 5,737,072 A | 4/1998 | Emery et al. | 356/73 |
| 5,748,305 A | 5/1998 | Shimono et al. | 356/237 |
| 5,774,222 A | 6/1998 | Maeda et al. | 356/394 |
| 5,781,230 A | 7/1998 | Nguyen et al. | 348/128 |
| 5,797,317 A | 8/1998 | Lahat et al. | 101/127.1 |
| 5,801,824 A | 9/1998 | Henley | 356/237 |
| 5,805,278 A | 9/1998 | Danko | 356/237 |
| 5,808,735 A | 9/1998 | Lee et al. | 356/237 |
| 5,818,576 A | 10/1998 | Morishige et al. | 356/237 |
| 5,822,213 A | 10/1998 | Huynh | 364/478.01 |
| 5,834,758 A | 11/1998 | Trulson et al. | 250/201.2 |
| 5,861,952 A | 1/1999 | Tsuji et al. | 356/349 |
| 5,864,394 A | 1/1999 | Jordan, III et al. | 356/237 |
| 5,883,710 A | 3/1999 | Nikoonahad et al. | 356/237.2 |
| 5,889,593 A | 3/1999 | Bareket | 356/445 |
| 5,903,342 A | 5/1999 | Yatsugake et al. | 356/237.4 |
| 5,909,276 A | 6/1999 | Kinney et al. | 356/237 |
| 5,912,732 A | 6/1999 | Sekine | 356/237.5 |
| 5,940,175 A | 8/1999 | Sun | 356/237.3 |
| 6,012,966 A | 1/2000 | Ban et al. | 451/8 |
| 6,020,957 A | 2/2000 | Rosengaus et al. | 356/237.4 |
| 6,236,903 B1 * | 5/2001 | Kim et al. | 700/121 |

FOREIGN PATENT DOCUMENTS

| | | | |
|---|---|---|---|
| EP | 1 030 173 A1 | 8/2000 | G01N/21/89 |
| EP | 1030173 A1 | 8/2000 | G01N/21/89 |
| EP | 1 083 424 A2 | 3/2001 | G01N/21/94 |
| JP | 09196859 | 7/1997 | G01N/21/88 |
| WO | 97/19416 | 5/1997 | G06K/7/10 |
| WO | 99/00661 | 1/1999 | G01N/21/64 |
| WO | 99/49500 | 9/1999 | H01L/21/00 |
| WO | WO 99/56113 | 11/1999 | G01N/21/89 |

OTHER PUBLICATIONS

European Search Report dated Dec. 12, 2000.

International Search Report for PCT/US01/42483, dated Oct. 14, 2002.

Search Report from EPO Appl. No. 00307704.7, dated Mar. 1, 2001.

International Search Report for PCT/US01/31426, dated Nov. 27, 2002.

International Search Report for PCT/US01/31094, dated Nov. 27, 2002.

PCT International Preliminary Examination Report, May 30, 2003.

U.S. patent application Ser. No. 09/173,669, *Detection of Wafer Fragments in a Wafer Processing Apparatus*, filed on Oct. 15, 1998.

* cited by examiner

PARTICLE DETECTION AND EMBEDDED VISION SYSTEM TO ENHANCE SUBSTRATE YIELD AND THROUGHPUT

This is a continuation of application Ser. No. 09/391,341, filed Sep. 7, 1999.

BACKGROUND OF THE INVENTION

FIELD OF THE INVENTION

The present invention relates to a method and apparatus for detecting the presence of defects, such as particles on a substrate surface. More particularly, the invention utilizes a combination of a light source and a detector to illuminate a substrate surface and detect scattered energy therefrom.

BACKGROUND OF THE RELATED INVENTION

Semiconductor processing generally involves the deposition of material onto and removal ("etching") of material from substrates. Typical processes include chemical vapor deposition (CVD), physical vapor deposition (PVD), etching and others. During the processing and handling of substrates, the substrates often become contaminated by particulates that can lodge themselves in the features of devices formed on substrates. Sources of contamination include wear from mechanical motion, degradation of seals, contaminated gases, other contaminated substrates, flaking of deposits from processing chambers, nucleation of reactive gases, condensation during chamber pumpdown, arcing in plasma chambers and so forth. As the geometries of device features shrink, the impact of contamination increases. Thus, current semiconductor manufacturing routinely includes inspection of substrates for particles to identify "dirty" processes or equipment.

In general, there are two commercial methods for detecting particle contamination on a substrate surface, one being an X-Y surface scan and another being a rotary type scan. In each case, an actuating mechanism, or stage, is used to move a substrate relative to light sources such as laser diodes. FIG. 1 is a perspective view of an exemplary inspection apparatus 10. A substrate 11 is positioned on a stage 13 capable of moving in an X-Y plane. In the case of a rotary type inspection device, the stage 13 is also capable of rotation about an axis. A light source 12 emits light beam 14 onto the substrate 11 and irradiates the surface. The light beam 14 is focused as a spot by condenser lens 15 to define an inspected area of the substrate 11. Particles, device patterns, and other protrusions on the upper surface of the substrate 11 cause the incident light beam 14 to scatter in various directions, as shown by arrows 16, according to the light incidence angle and geometry of the protrusions. The scattered light 16 is received by a collector lens 18 and then transmitted to a detector 20 positioned in proximity to the substrate 11. The detector 20 is typically a Photo-Multiplier Tube (PMT), a charge-coupled device (CCD) or other light sensitive detector. The detector 20 converts the scattered light 16 into a signal corresponding to the detected protrusions on the substrate surface. The signal is routed to a processing unit 22 to generate data regarding various parameters of interest such as the size and location of the detected protrusions. This approach, wherein scattered light from a surface under observation is detected, is known as "Dark Field Illumination." Dark Field Illumination implies that only light scattered by protrusions on the substrate surface is detected and light which is merely reflected by the planar substrate surface is disregarded.

One disadvantage with conventional inspection systems is the prohibitive size and cost of the systems. Current systems are typically expensive stand-alone platforms that occupy additional clean-room space. As a result of the large area, or "footprint," required by the stand-alone inspection platforms, the cost of owing and operating such a system is high. One reason for the size of the inspection systems is the desire for highly sensitive equipment capable of detecting sub-micron particles. In order to achieve such sensitivity, vibration due to the various moving components of the platform such as the stage, which interfere with the inspection techniques, must be eliminated. Thus, the inspection platforms are stabilized using a massive base comprising, granite slab, for example, to minimize the effects of vibration. To accommodate the wide range of motion of the stage and the massive base, conventional platforms occupy a large footprint in a fabrication facility (fab), thereby increasing the cost of operation of the overall fab.

Another problem with current inspection devices is the negative impact on throughput, or productivity. As described above, a stage moves a substrate through an X-Y plane to position the substrate relative to the light source. Conventional inspection platforms, such as the one in FIG. 1, illuminate only a small portion, or spot, on the substrate being inspected. The substrate is then moved repeatedly by the stage to expose the entire surface of the substrate to the light source. Consequently, conventional platforms drastically increase overhead time associated with chip manufacturing. One attempt to reduce the overhead time and increase throughput in a reticle inspection using a stage is shown in U.S. Pat. No. 5,663, 569 which utilizes optics capable of shaping the light beam into a line, or slit, to allow for single-pass inspection. The slit dimensions are adjusted to accommodate the width of the object under inspection so that the object need only be scanned in a single direction once. However, the light source is positioned to obliquely irradiate the reticle, thereby producing a non-uniform spot pattern. Specifically, the light source is offset to one side of the reticle such that the reticle moves past the light source during a scan as opposed to toward or away from the light source. As a result, the light produces a more intense pattern on the portion of the reticle closer to the light source while a less intense pattern is produced farther away from the light source.

Throughput is further diminished because the current inspection systems are stand-alone platforms that require substrates to be removed from the vacuum environment of the processing system and transferred to the separate inspection platform. Thus, production is effectively halted during transfer and inspection of the substrates. Further, because such an inspection method is conducive only to periodic sampling due to the negative impact on throughput, many contaminated substrates are processed before inspection and detection of problems occurs. The problems with substrate inspection can be compounded in cases where the substrates are re-distributed from a given batch making it difficult to trace the contaminating source.

It would be preferable to have an inexpensive in situ inspection method and apparatus incorporated into existing processing systems capable of detecting particles on substrates. Further, the preferred inspection apparatus should be capable of being retrofitted to existing processing systems. The inspection apparatus should be positioned to allow inspection of each substrate before and/or after processing. Impact to throughput should be minimized by inspecting substrates "on-the-fly" during transfer between typical processing steps without the need for a separate inspection platform and stage.

Another problem with particle detection systems is the noise produced by chip patterns formed on substrates. During inspection by conventional illumination techniques, the patterns act as micro-mirrors causing the light to reflect in various directions. As a result, the patterns may produce misleading information, i.e., the patterns may indicate the presence of foreign particles where none are found. In order to allow particle detection of patterned substrates various methods and apparatus have been implemented in the art.

U.S. Pat. No. 5,463,459, entitled "Method and Apparatus for Analyzing the State of Generation of Foreign Particles in Semiconductor Fabrication Process," provides a method of detecting foreign particles on a substrate by "eliminating" the patterns formed on the substrate. For example, corresponding portions of adjacent chips are compared to determine differences. The chips are illuminated with a light source to cause reflection of the light which is detected by detection equipment while the substrate is actuated by a conventional stage. The reflected distribution of light is then compared to determine the presence of foreign particles on the substrate. The portion of the resulting signals which are identical are erased leaving only differences in the signals. The differences are assumed to be the result of particles on the substrate.

While such a method can achieve relatively high resolution capable of detecting sub-micron particles, the necessary equipment and signal processing systems are complex and expensive as well as time-consuming because in order to produce high resolution detection long scanning times are needed. Further, sources of foreign particles can produce large-scale particles, therefore, small-scale particle detection may not be necessary in cases where catastrophic chamber failures occur. By "catastrophic" is meant flaking of material that has accumulated on the chamber surfaces.

Therefore, what is needed is a system capable of rapidly determining the condition of a substrate in order to facilitate a subsequent substrate handling decision. That is, a preferred detection system would allow a quick decision to be made about whether an additional and more precise particle detection analysis is necessary. Preferably, the system would also allow the substrate inspection to be performed on-the-fly and produce real-time data on each substrate undergoing processing, rather than just arbitrarily selected substrates from a batch. Such a preferred system would maximize the system throughput and reduce operating costs by eliminating the need for time-consuming inspection of small-scale particles and also the cost associated therewith.

Therefore, there is a need for an integrated particle detection system which allows for on-the-fly monitoring and the detection of particles in a processing system.

SUMMARY OF THE INVENTION

The present invention generally provides a particle detection apparatus in a processing system. In one aspect of the invention, a transmitter unit and a receiver unit are disposed on or near a chamber and cooperate to transmit and detect energy. The transmitter unit is positioned to transmit a signal onto a moving substrate surface. The receiver unit is positioned to collect a scattered portion of the signal and direct the same to a processing unit.

In another aspect of the invention, a transmitter unit and a receiver unit are disposed on a semiconductor processing system and cooperate to transmit and detect energy, respectively. The transmitter unit is positioned to transmit a signal into a region of the processing system, such as a transfer chamber, and onto a substrate surface moving therethrough.

In one embodiment, the signal is transmitted onto a substrate moving through a cavity of the transfer chamber and preferably between the transfer chamber and an adjacent vacuum chamber. A robot preferably located in the transfer chamber or a front-end environment of the processing system, enables movement of the substrate. The receiver unit is disposed to collect a scattered portion of the signal and direct the same to a processing unit. Preferably, the transmitter unit and the receiver unit are disposed in a region external to the processing system.

In yet another aspect of the invention, a light source and one or more charge-coupled devices (CCD) are disposed on or near a chamber and cooperate to transmit and detect energy, respectively. The laser source is positioned to transmit a signal onto a moving substrate surface. The CCD is disposed to collect a scattered portion of the signal and direct the signal to a processing unit.

In still another aspect of the invention, a signal is transmitted on a substrate moving in a first direction between a first vacuum chamber and a second vacuum chamber of a semiconductor processing system or rotationally within the first chamber. Preferably, the first vacuum chamber is one of a transfer chamber or a front-end environment and the second vacuum chamber is one of a process chamber, a service chamber or a load lock chamber. A reflected portion of the signal is received by a receiver unit and subsequently directed to a processing unit for processing. In one embodiment, the reflected portion of the signal is reflected by particles disposed on the substrate. In another embodiment, the reflected portion of the signal is reflected by alphanumeric characters disposed on the substrate.

In still another aspect of the invention, a signal is transmitted on a substrate moving in a first direction between a first and second vacuum chamber of a semiconductor processing system or rotationally within the first chamber. Preferably, the first vacuum chamber is one of a transfer chamber or a front-end environment and the second vacuum chamber is one of a process chamber, a service chamber or a load lock chamber. A reflected portion of the signal is received by a receiver unit and subsequently directed to a processing unit for processing. The processing unit is adapted to read a computer-readable program product to generate information pertaining to the substrate. Preferably, the program product is adapted to provide substrate positional information, substrate reflectivity information, specular information, substrate defect information, substrate damage information, particle contamination information for the substrate support member and a substrate disposed thereon, alphanumeric character information, robot behavior information, calibration information for a robot, a transmitter unit and/or a receiver unit, and any combination thereof.

In still another aspect of the invention, a method of determining the center and/or orientation of a substrate is provided. A substrate is positioned in a chamber having a receiver unit and transmitter unit disposed therein. The surface of the substrate is illuminated with radiation from the transmitter unit and an image representative of at least an edge portion of the substrate is captured by the receiver unit. The image is analyzed to determine at least one of the center or orientation of the substrate. The substrate surface illuminated may be the backside of the substrate or the upper surface of the substrate in facing relation to the receiver unit.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

The present invention generally provides a particle detection apparatus in a processing system. A transmitter unit and a receiver unit are disposed on or near a chamber and cooperate to transmit and detect energy. The transmitter unit is positioned to transmit a signal onto a substrate surface moving between vacuum chambers. Particles disposed on the substrate surface cause a scattering of a portion of the signal. The receiver unit is positioned to collect and measure the scattered portion of the signal and direct the same to a processing unit. Preferably, the transmitter unit comprises a light source and the receiver unit comprises a charged-coupled device (CCD).

Figure 2:
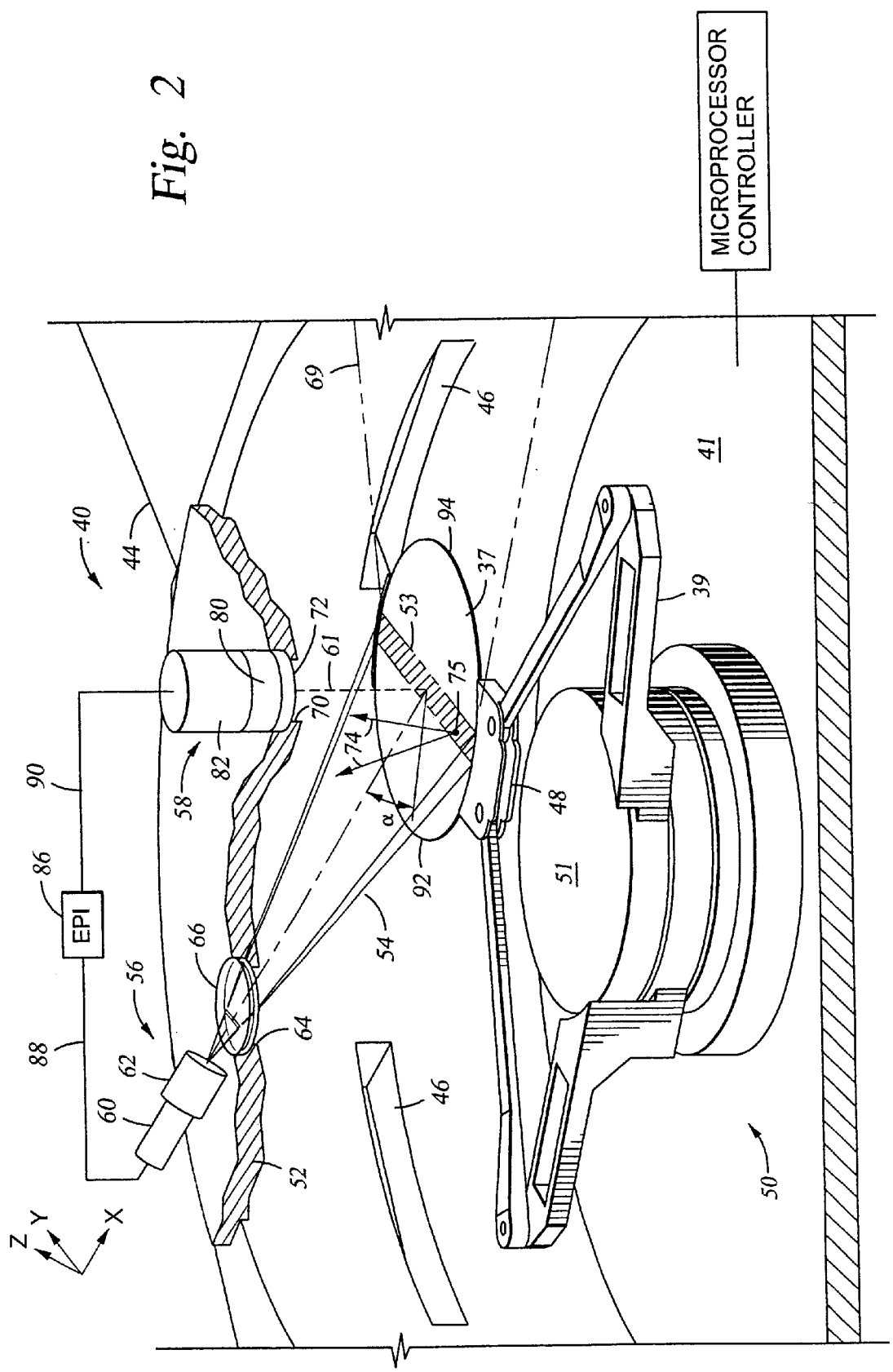
FIG. 2 is a partial perspective view of a processing system.
Figure 3A:
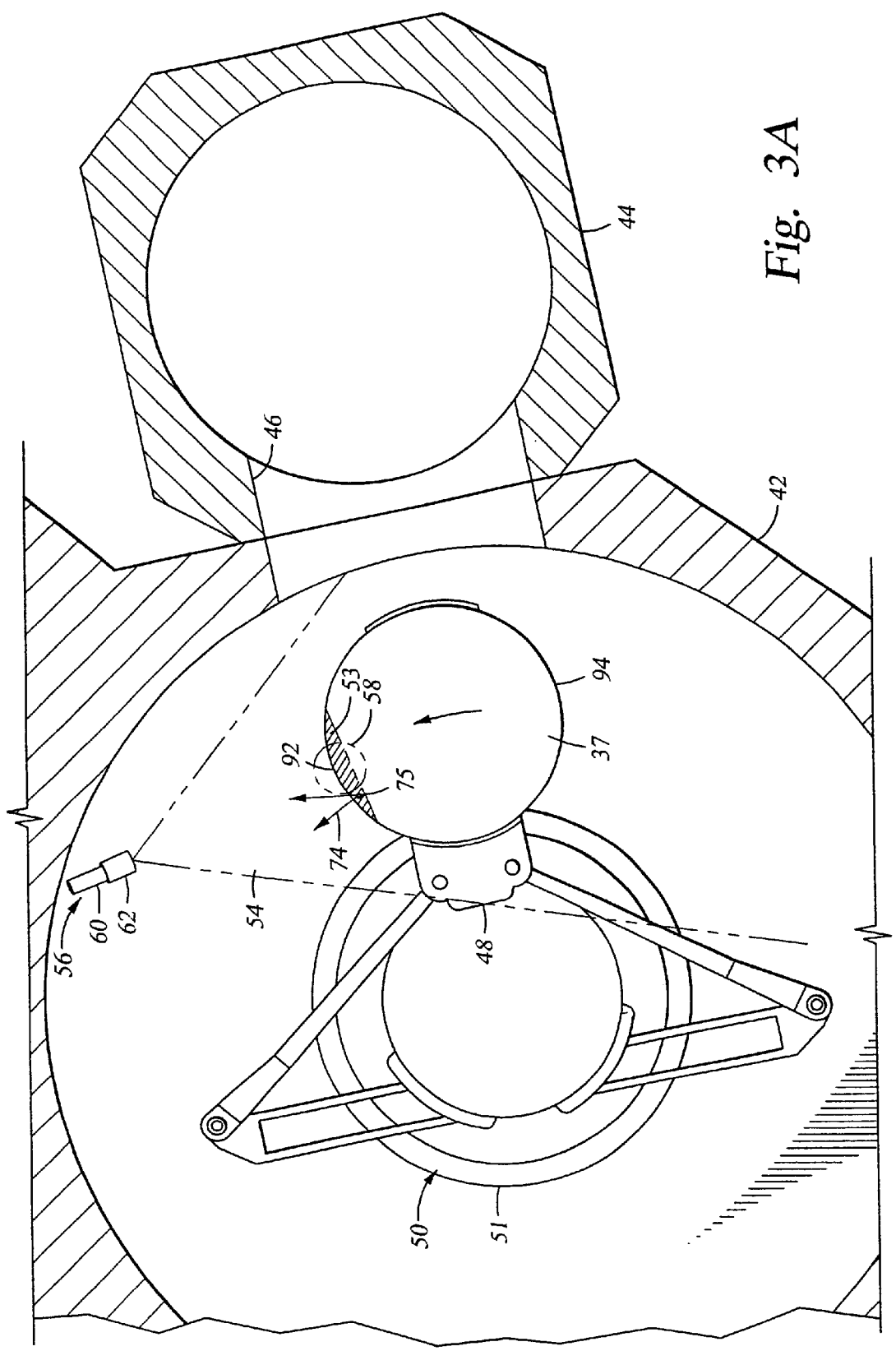
FIGS. 3A–C are top views of the processing system of FIG. 2 showing various positions of a substrate disposed on a blade during rotation of the blade.

FIG. 2 is a perspective cutaway of a processing system 40 of the present invention comprising a transfer chamber 42 and a vacuum chamber 44 mounted thereon (see FIG. 3A). The transfer chamber 42 and the vacuum chamber 44 are selectively communicable through an aperture 46 which can be sealed by a conventional apparatus such as a slit valve door (not shown). The aperture 46 is sized to accommodate the transfer of substrates therethrough. A robot 50 is centrally disposed in the transfer chamber 42 and comprises a blade 48 coupled to the robot hub 51 by frog-leg type linkage 39. The robot 50 enables rotational and radial movement of the blade 48 along a transfer plane, thereby shuttling substrates between various positions. The transfer chamber 42 and the vacuum chamber 44 are preferably components of a cluster tool 100 such as the one shown in FIG. 5 and described in detail below. Thus, the vacuum chamber 44 may be a load lock chamber providing an interfacing chamber between a front-end environment and the transfer chamber 42, while the transfer chamber 42 provides a vacuum environment communicable with various peripheral chambers. Alternatively, the vacuum chamber 44 may be a process chamber.

As shown in FIG. 2 a transmitter unit 56 and a receiver unit 58 are externally mounted to a lid 52 of the transfer chamber 42. The transmitter unit 56 includes a light source 60 and beam-shaping optics 62 and is positioned to emit a signal 54 into the cavity 41 of the transfer chamber 42 via a view port 64. The view port 64 comprises an opening formed in the lid 52 and is hermetically sealed with plate 66 made of a material transparent to the signal 54 of the light source 60. In one embodiment, the plate 66 may comprise Pyrex™, for example. In operation, the signal 54 propagates parallel to the x-axis shown in FIG. 2 and is directed onto an upper surface of a substrate 37 rotating through the cavity 41 of the transfer chamber 42. The signal defines a light pattern 53 upon falling on the substrate 37. As described in detail below, the spot size of the light pattern 53 may be varied according the substrate size by adjusting the beam shaping optics 62 and the position of the light source 60.

The light source 60 can be, for example, a laser source or a broad spectrum light source. In general, the light source 60 is selected according scattering intensity, brightness and cost. Where a laser source is used, the laser source is preferably operable at about 808 nm. However, other laser sources, such as 650 nm or 680 nm wavelength laser sources, may also be used.

In general, the spot size of the light pattern 53 is substantially determined by the beam-shaping optics 62 and the position of the transmitter unit 56. The beam-shaping optics 62 is selected to provide a spot size according to the dimensions of the substrate. For a 300 mm substrate, for example, the spot size of the light pattern 53 is preferably at least 220 $\mu$m (width)×300 mm (length, y-axis) on the upper surface of a substrate. Thus, in operation, the entire breadth of a 300 mm substrate is exposed to the signal 54 after a single scan. However, it is believed that only 60% or more of the substrate need be exposed to the signal 54. Typical sources of catastrophic process chamber contamination, such as flaking (also known as chamber excursions), provide hundreds of particles that may settle on the processing surface of a substrate. Successful particle detection requires only that a portion of the contaminants be detected to confirm the presence of a contaminated substrate. Thus, monitoring at least 60% of the processing surface ensures a substantial probability of detecting a contaminated substrate.

Referring still to FIG. 2, the receiver unit 58 is shown mounted in a view port 70 formed in the lid 52 and defines an optical path 61 toward the substrate 37 moving through the cavity 41. The receiver unit 58 is secured above an energy transparent plate 72 made of a material selected according to the operating wavelength of the signal 54 and preferably comprises of the same material as the plate 66 disposed in view port 64. For example, where the light source 60 is a laser source operating at about 808 nm, the material for the plates 66, 72 is selected to accommodate a 808 nm signal. The receiver unit 58 is positioned to receive a scattered portion 74 of the signal 54 from the substrate 37 during operation. The scattered portion 64 is represented by a multiplicity of arrows oriented at various angles relative to the upper surface of the substrate 37 and indicates the presence of an obstruction, such as particulate contamination disposed on the upper surface of the substrate 37. A reflected portion 69 of the signal 54 propagates at angle relative to the substrate 37 substantially equal to the angle of incidence α. The reflected portion 69 represents the portion of the signal 54 substantially unobstructed upon intercepting the upper surface of the substrate 37.

The receiver unit 58 includes an optics assembly 80, comprising one or more lens, and a detector 82. The detector 82 of the receiver unit 58 preferably comprises a charge-coupled device (CCD) line camera. A CCD line camera is a preferred detector due to its high immunity to out-ofsubstrate noise and its ability to provide particle coordinates on a substrate. By using a line CCD the vertical coordinate of each detected particle can be determined. However, while CCD detectors are preferred, other detectors, including time delay integration (TDI) detectors, or PMT's may be used to advantage. Where a TDI detector is used the spot is adjusted to correspond to the TDI size as is known in the art.

The foregoing description for positioning the transmitter unit 56 and receiver unit 58 is merely illustrative and other embodiments are possible. For instance, while FIG. 2 shows the transmitter unit 56 and the receiver unit 58 disposed outside the cavity 41 of the transfer chamber 42, in another embodiment the transmitter unit 56 and the receiver unit 58 are positioned inside the cavity 41, and thus, under vacuum conditions. Additionally, as will be described in detail below, the invention has application other than particle detection and, therefore, can be modified accordingly.

Together, the transmitter unit 56 and the receiver unit 58 comprise an Optical Sensor Assembly (OSA). The operation of the OSA is controlled by an Electronic Processing and Interface Unit (EPI) 86. As shown in FIG. 2, the EPI 86 is electrically coupled to the transmitter unit 56 by an input cable 88 and provides command signals thereto and is electrically coupled to the receiver unit 58 by an output cable 90 to receive output signals therefrom. Although the microprocessor/controller for the processing system 40 is preferably separate from the EPI 86, in one embodiment the EPI 86 may serve as the control unit for the processing system 40, thereby eliminating the need for an additional control unit.

The EPI 86 may be operated using a computer program product comprising a computer code, which can be run on a conventional computer. The computer program can be written in any conventional computer readable programming language such as, for example, 68000 assembly language, C, C++, Pascal or Java. Suitable program code is entered into a single file, or multiple files, using a conventional text editor, and stored or embodied in a computer usable medium, such as a memory system of the computer. If the entered code text is in a high level language, the code is compiled, and the resultant compiler code is then linked with an object code of precompiled windows library routines. To execute the linked compiled object code, the system user invokes the object code, causing the computer system to load the code in memory from which the CPU reads and executes the code to perform the tasks identified in the program.

Upon initiation by a user, the EPI 86 continues to monitor substrates which enter the field of view of the receiver unit 58. If the EPI 86 detects the presence of a contaminated substrate, the user may be alerted by a warning message displayed on a display unit (not shown). Additionally or alternatively, the microprocessor/controller of the processing system 40 can be instructed by the EPI 86 to transfer the substrate to a particular location for eventual disposal, cleaning or further inspection.

Figure 3B:
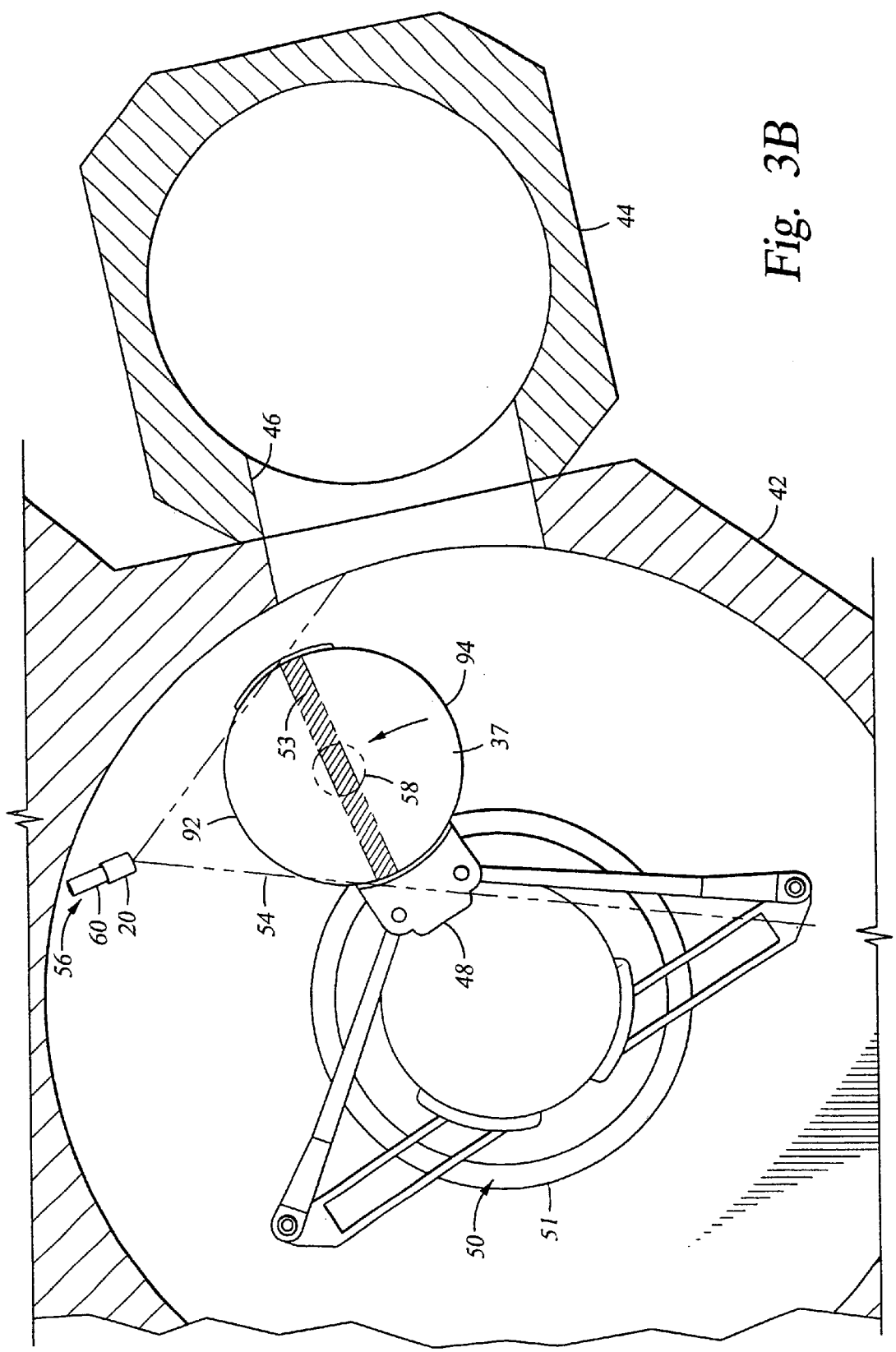
Figure 3C:
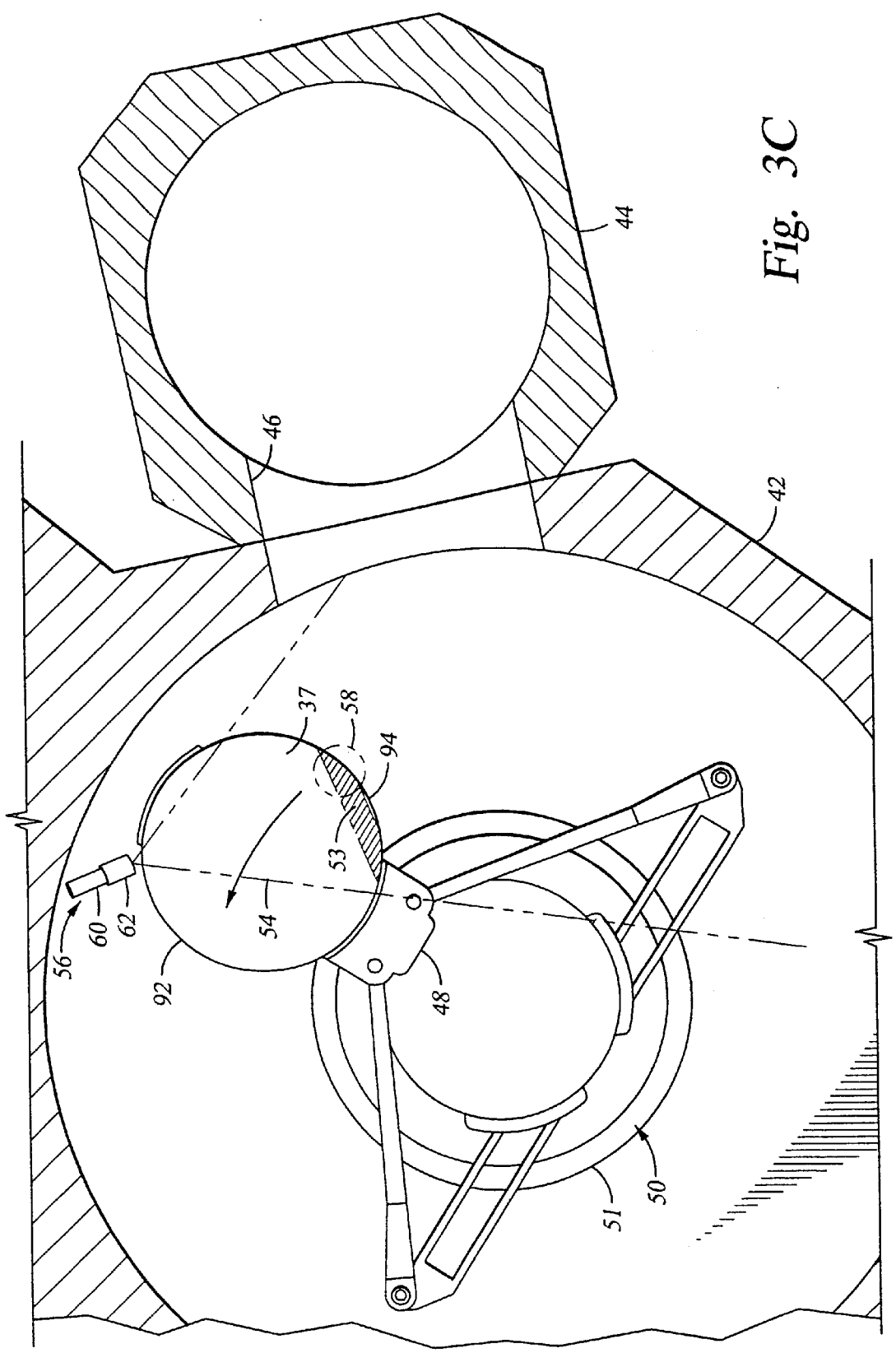

The operation of the present invention is illustrated by FIGS. 3A–C. FIGS. 3A–C are top views of the processing system 40 showing the blade 48 and substrate 37 in various positions during rotation through the transfer chamber 42. FIG. 3A shows the blade 48 immediately after initiating counter-clockwise rotation so that the leading edge 92 of the substrate 37 is positioned in the path of the signal 54. Thus, a portion of the light pattern 53, represented by the shaded area, is shown intercepting the leading edge 92 of the substrate 37. During the continued rotation of the blade 48, shown by FIGS. 3B–C, the light pattern 53 scans the upper surface of the substrate 37. The light pattern 53 illuminates particles 75 on the substrate 37 which causes scattering of the signal 54. The size of the particles 75 are typically in the micron range but are shown greatly exaggerated for clarity. The scattered portion 74 of the signal 54 is then collected by the receiver unit 58. Where the detector 82 is a CCD, the scattered portion 64 is focused by the receiver optics 80, imaged onto the elements of the CCD, converted into an electrical signal and transmitted to the EPI 86 for processing.

It is understood that the foregoing sequence may be performed before and/or after the substrate 37 undergoes a processing cycle in a processing chamber. For example, FIGS. 3A–C may represent a substrate being transferred from a load lock chamber to a processing chamber. Alternatively, FIGS. 3A–C may represent a processed chamber being transferred to a cooldown chamber or being returned to a load lock.

Figure 4:
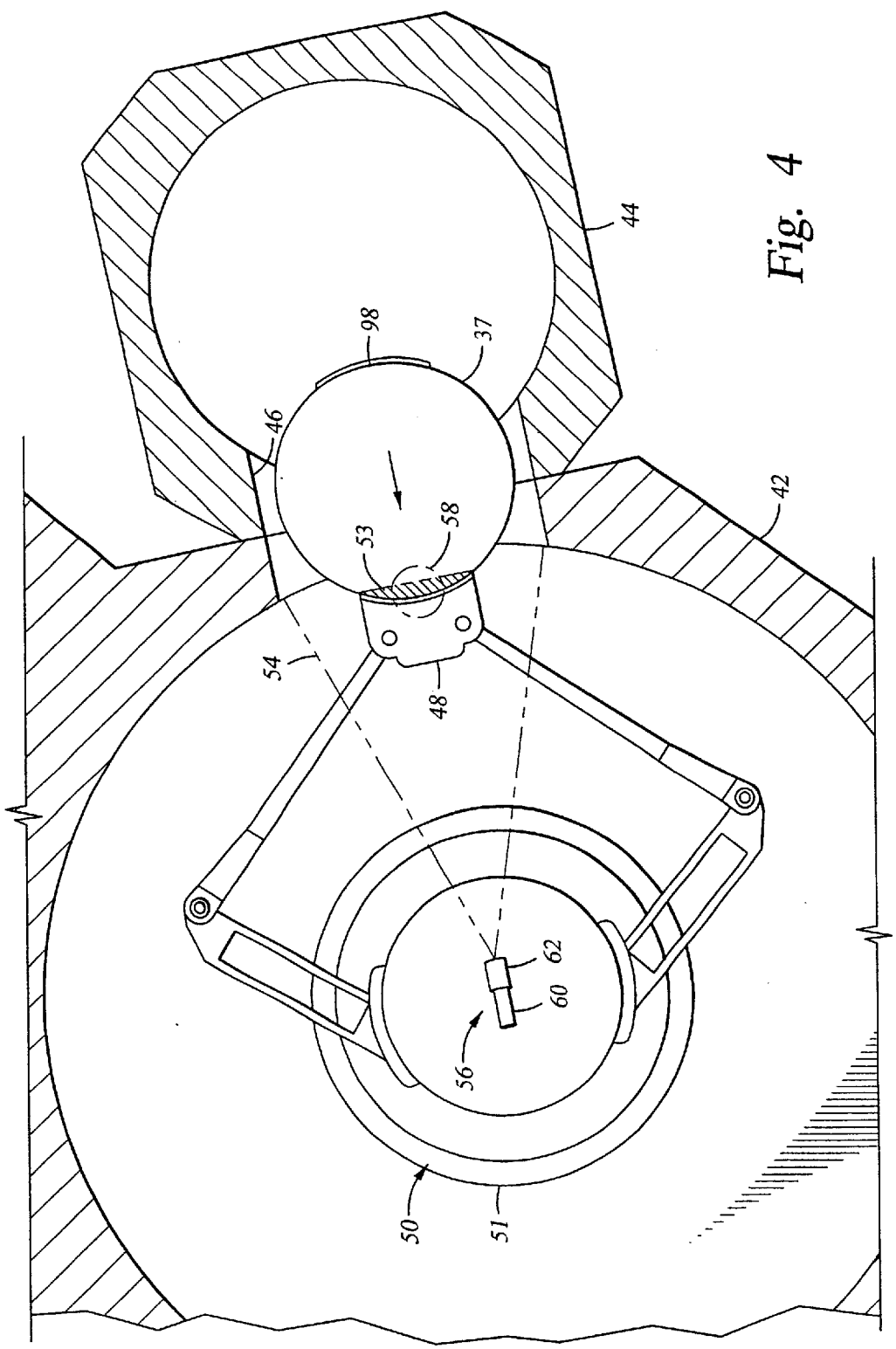
FIG. 4 is a top view of the processing system of FIG. 2 showing a substrate disposed on a blade during retraction of the blade.

While FIGS. 2 and 3A–C show the preferred positioning and operation for the transmitter unit 56 and receiver unit 58, other embodiments may be used to advantage. In general, the transmitter unit 56 and receiver unit 58 may be positioned at any point on the processing system 40 where the signal 54 may be directed onto the upper surface of a moving substrate and scattered light may be detected by the receiver unit 58. Thus, in another embodiment, particle detection is performed during retraction or extension of the robot 50 as describe with reference to FIG. 4. FIG. 4 is a top of the processing system 40 showing the blade 48 and substrate 37 disposed thereon during the retraction of the blade 48 from the vacuum chamber 44 into the transfer chamber 42 via the aperture 46. In order to maximize the exposed surface area of the substrate 37, the signal 54 preferably intercepts the substrate 37 in extreme proximity to the aperture 46 as shown in FIG. 3A. Such a positioning ensures exposure of substantially the entire upper surface of the substrate after full retraction of the blade 48, thereby maximizing the surface area of the substrate 37 which is scanned by the signal 54. The shaded portion of the light pattern 53 indicates the portion of the signal 54 incident on the substrate 37. As the blade 48 continues to retract, the substrate 37 is moved through the path of the signal 54, thereby exposing the upper surface of the substrate 37 to the signal 54. Particles 75 disposed on the upper surface of the substrate 37 cause the signal 54 to scatter, shown by arrows 74. The scattered portion of the signal 54 is collected by the receiver unit 58, converted into an electrical signal and transmitted to the EPI 86 for processing. Upon complete retraction of the blade 48, the light pattern 53 is preferably radially outward of the trailing edge 98 of the substrate 37 so that the full surface area of the substrate 37 has been exposed to the light pattern 53.

The embodiments shown in FIGS. 3A–C and 4 are merely illustrative. In an alternative embodiment, a pair of transmitter units 56 and receiver units 58 may be used in combination to monitor a substrate during linear motion and rotational motion, respectively. Such an arrangement can improve the accuracy of detection. A person skilled in the art will recognize other embodiments. Further, while a single surface scan of the substrate 37 provides a high degree of accuracy relative to particle detection, additional methods may be employed to enhance detection confidence. For example, the robot blade 48 may be dithered, or oscillated, so that a given particle can be moved into the field of view of another CCD detector element in the array of elements. Detection by multiple elements provides additional certainty of the existence and location of the particle.

Determination of the location of a particle on the substrate is made by identifying particular features on the substrate or blade. For example, in one embodiment the EPI may be programmed to detect the leading edge, i.e., the substrate curvature which first enters the field-of-view of the receiver unit, and lagging edge, i.e., the last curvature to be detected by the receiver unit, during linear or rotational movement of the substrate. The substrate edges provide reference points which may then be used to generate one of two coordinates, i.e., X and Y because the acquisition rate of the CCD detector is known. The acquisition rate refers to the frequency of image generation during the movement of the substrate in the field-of-view of the CCD detector. Preferably, consecutive image are generated so that no overlapping or missing portion of the substrate results. Thus, the processed output of the CCD detector is a "photograph" of the complete substrate surface. The remaining coordinate is determined by where the particle is detected on the detector array of the CCD detector.

The present invention has particular advantages in a multi-chamber processing system. One exemplary multi-chamber processing system commonly used in the semiconductor industry, well suited for supporting the detection apparatus described herein, is known as a cluster tool. A cluster tool is a modular system comprising multiple chambers which perform various functions including substrate center-finding and orientation, degassing, annealing, deposition and/or etching. The multiple chambers are mounted to a central transfer chamber which houses a robot adapted to shuttle substrates between the chambers. The transfer chamber is typically maintained at a vacuum condition and provides an intermediate stage for shuttling substrates from one chamber to another and/or to a load lock chamber positioned at a front end of the cluster tool. The centralized position of the transfer chamber provides an ideal location for a particle detection system.

Figure 5:
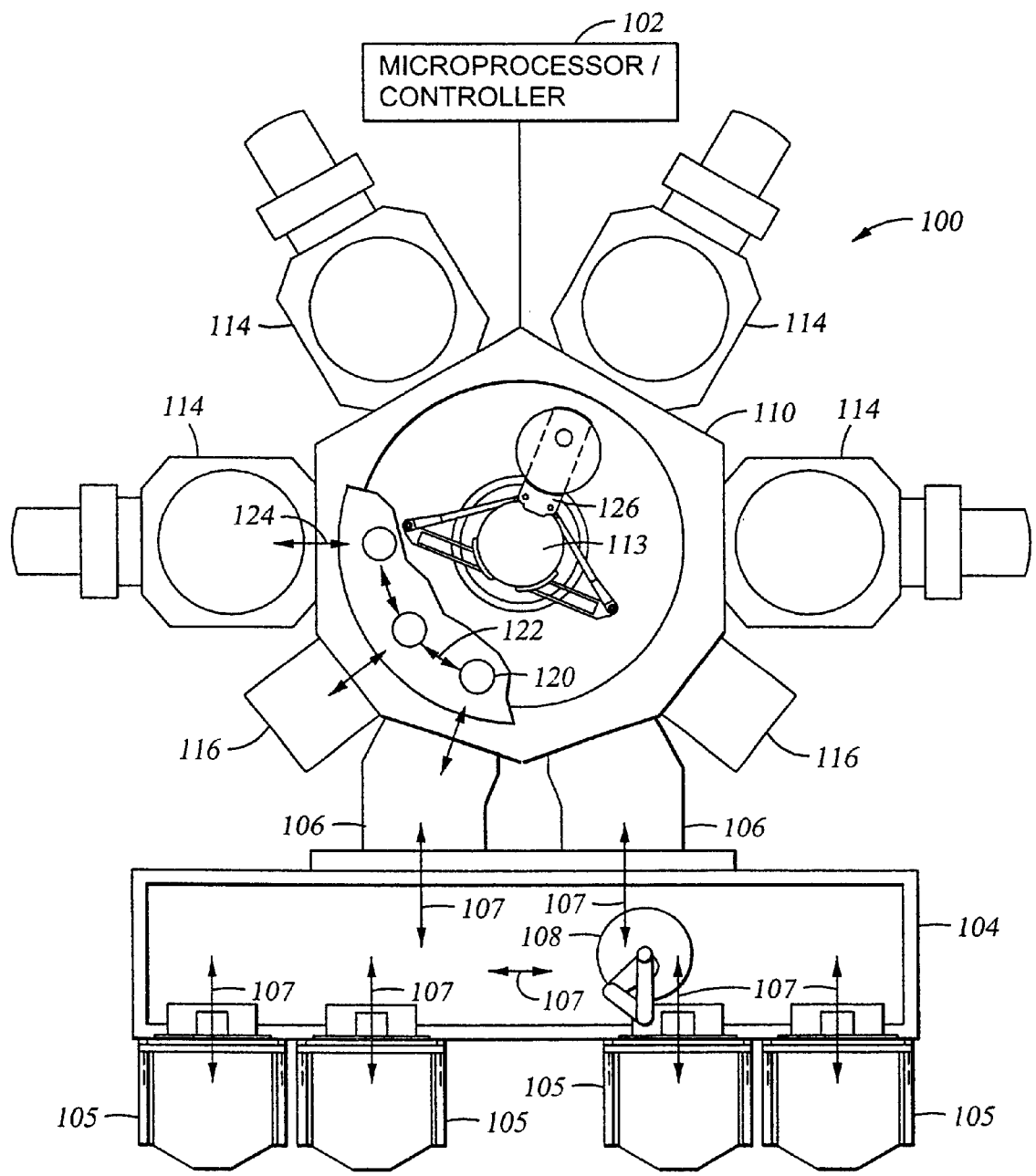
FIG. 5 is a plan view of a typical cluster tool for semiconductor processing.

Thus, the transfer chamber 42 and the vacuum chamber 44 may each be part of a cluster tool. FIG. 5 is a plan view of a typical cluster tool 100 for semiconductor processing wherein the present invention may be used to advantage. Two such platforms are the Centura® and the Endura® both available from Applied Materials, Inc., of Santa Clara, Calif. The details of one such staged-vacuum substrate processing system is disclosed in U.S. Pat. No. 5,186,718, entitled "Staged-Vacuum Wafer Processing System and Method," Tepman et al., issued on Feb. 16, 1993, which is incorporated herein by reference. The exact arrangement and combination of chambers may be altered for purposes of performing specific steps of a fabrication process.

In accordance with the present invention, the cluster tool 100 generally comprises a plurality of chambers and robots and is preferably equipped with a microprocessor controller 102 programmed to carry out the various processing methods performed in the cluster tool 100. A front-end environment 104 is shown positioned in selective communication with a pair of load lock chambers 106. A pod loader 108 disposed in the front-end environment 104 is capable of linear and rotational movement to shuttle cassettes of substrates between the load locks 106 and a plurality of pods 105 which are mounted on the front-end environment 104. The load locks 106 provide a first vacuum interface between the front-end environment 104 and a transfer chamber 110. Two load locks 106 are provided to increase throughput by alternatively communicating with the transfer chamber 110 and the front-end environment 104. Thus, while one load lock 106 communicates with the transfer chamber 110, a second load lock 106 communicates with the front-end environment 104. A robot 113 is centrally disposed in the transfer chamber 110 to transfer substrates from the load locks 106 to one of the various processing chambers 114 and service chambers 116. The processing chambers 114 may perform any number of processes such as physical vapor deposition, chemical vapor deposition, and etching while the service chambers 116 are adapted for degassing, orientation, cooldown and the like.

A number of view ports 120 provide visual access into the transfer chamber 110. The view ports 120 provide suitable locations for the transmitter unit 56 and the receiver unit 58. Arrows 122, 124 indicate points where inspection of a substrate may be preformed. Arrows 122 represent points where the robot blade 126 is rotated and arrows 124 represent points where the robot blade 126 is extended or retracted. The transmitter unit 56 and receiver unit 58 may be positioned in the view ports 120 accordingly as described with reference to FIGS. 2–4. For example, the transmitter unit 56 and receiver unit 58 may be secured above the view port 20 in a position having field of view of the robot blade 126 entering or exiting the load lock 106. As noted above, the use of more than one transmitter unit 56 receiver unit 58 pair is also contemplated by the present invention. While the foregoing has been described with reference a to the transmitter unit 56 and the receiver unit 58 disposed on the transfer chamber 110, the invention has application at any position in the cluster tool 100 where substrate are in motion. Thus, arrows 107 indicate the movement of substrates through other locations in the cluster tool 100 which provide additional inspection sites.

Figure 1:
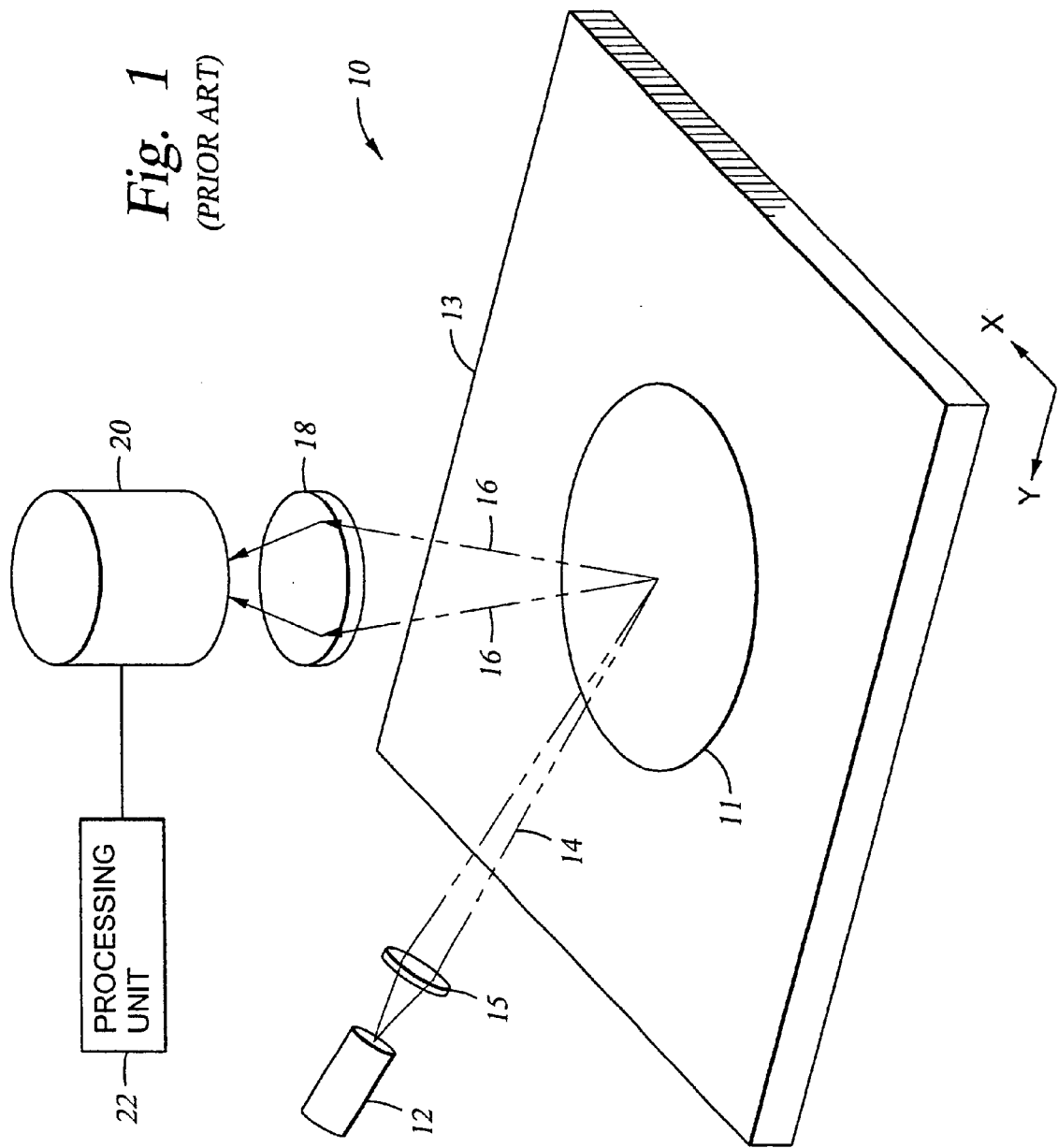
FIG. 1 is perspective view of a prior art inspection apparatus.

The foregoing embodiments provide a detection apparatus and method capable of detecting the presence of particles on substrates on-the-fly and in situ. In situ, on-the-fly detection eliminates the need for conventional stand-alone inspection platforms comprising dedicated actuating mechanisms such as the stage 13 shown in FIG. 1. The present invention-uses to advantage components typically included in any conventional processing system, such as the robot 50 (shown in FIGS. 2–4), to enable a stageless inspection system. Particle detection is performed at various positions in a processing system during normal and necessary operation sequences without transferring the substrates to a separate stand-alone inspection platform, thereby minimizing the impact on throughput. Consequently, each substrate entering or exiting the process system can be inspected, thereby achieving a significant improvement over prior art wherein only periodic sampling was possible due to the negative effect on overhead time. Further, the use of conventional features such as view ports and transfer robots facilitates retrofitting the present invention to existing systems without the need for expensive re-machining procedures.

For simplicity, the foregoing has been directed toward particle detection on unpatterned substrates having substantially smooth planar surfaces. On unpatterned substrates, light from the light source 60 (shown in FIG. 2) is scattered only upon striking a particle. Patterned substrates however include topological variances that can cause scattering of incident light, thereby falsely indicating the presence of a particle. Thus, where patterned substrates are to be examined, the invention utilizes a unique signature produced by illuminating each substrate in order to differentiate between substrates. The unique signature is the result of the patterns formed on the substrate. Because the topology due to patterns of substrates that undergo a particular process is substantially repetitive, the signature will be unique for each of the substrates. Thus, the unique signature may be stored in a memory and used to compare surface conditions of substrates during production.

Figure 6:
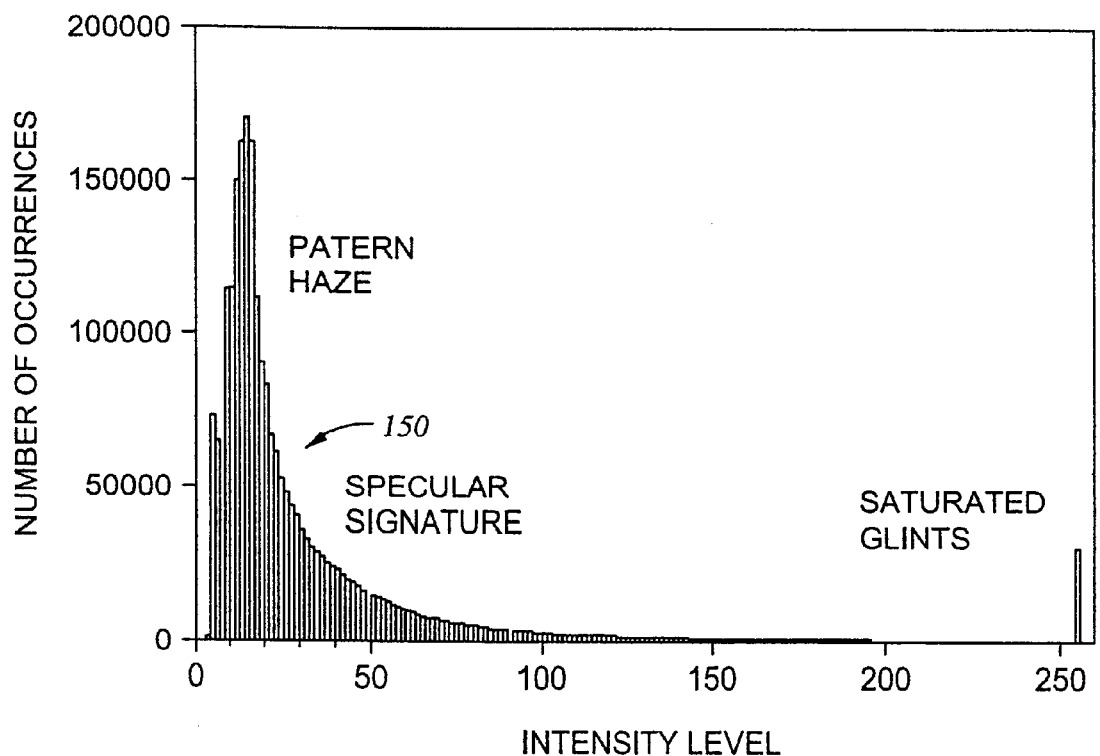
FIG. 6 is a graphical representation of specular reflections on a patterned substrate illuminated by a light source.
Figure 7:
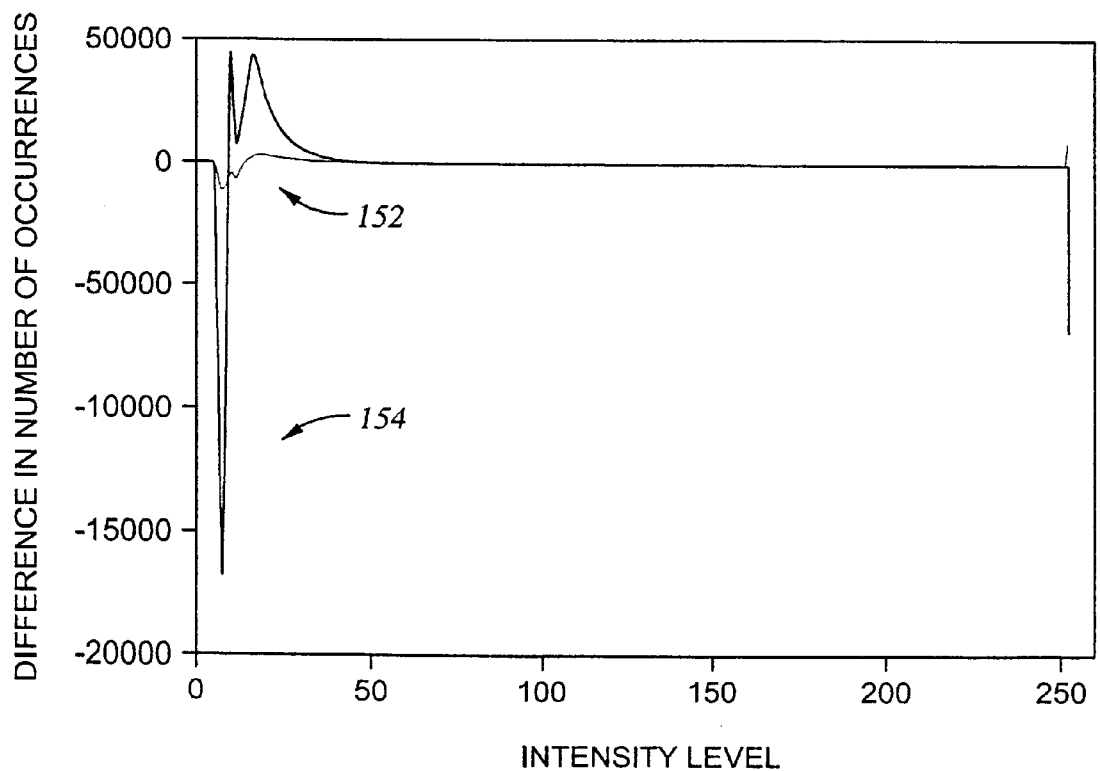
FIG. 7 is a comparative graphical representation of specular reflections on patterned substrates.

FIG. 6 represents a scan of 3 million data points showing the specular "signature" 150 for a calibration substrate scanned according to the techniques described above. The number of occurrences (y-axis), or readings by the detection equipment, at a particular intensity (x-axis) are plotted. Subsequently, two different test substrates were scanned in a similar manner resulting in two separate and distinct spectral signatures. To determine the relative conditions of the surfaces of the substrates, the signatures for the two test substrates were compared to the signature 150 for the calibration substrate. The graphs 152, 154 shown in FIG. 7 are the result of subtracting the number of occurrences at a given intensity for the calibration substrate from the number of occurrences at the same given intensity for the two test substrates. Thus, a first graph 152 represents the difference in the recorded output of the detection equipment between the first test substrate and the calibration substrate and shows little variation. A second graph 154 represents the difference in the recorded output of the detection equipment between the second test substrate and the calibration substrate and shows a significant variation, indicating a difference in the surface conditions of the compared substrates.

Thus, the invention provides an efficient and effective method of comparing substrate surface, conditions on-the-fly in a processing system. In production, the invention is a viable method of determining whether production should be halted and a particular substrate should be examined more carefully for contamination or defects. Only selected substrates need undergo additional particle detection, thereby minimizing the impact to throughput.

In addition to particle detection, a preferred device would be capable of performing other functions typically performed in a processing chamber and inspection chamber in order to increase throughput and decrease operating cost. In the production of devices it is necessary to determine various characteristics of a substrate of which particle contamination is only one. For example, substrate characteristics such as discontinuity (the presence of fractures and other structural defects) are important to identify potential problems which may affect the efficient operation of a system and lead to increased cost of operation due to damaged substrates. Additionally, substrate centerfinding and orientation are often necessary steps during processing to generate positional information regarding substrates. In conventional systems such procedures are performed at designated locations in the processing system. Thus, a substrate must be shuttled to the designated locations in order to undergo each procedure, thereby decreasing throughput. Further, because such tests are typically performed only periodically on an arbitrary substrate, many substrates may be damaged before a problem is identified.

Another situation which can cause increased processing costs is improper substrate routing. Occasionally, a substrate may be improperly routed to a process chamber where the processing conditions cause a volatile reaction, thereby damaging the substrate and/or the processing chamber. Because current processing systems are not equipped to prevent misrouting, the cost of operation is increased.

Thus, what is needed is a "gate-keeper" apparatus and method capable of examining a substrate for selected characteristics which include particles, orientation, centerfinding, reflectivity, substrate type, discontinuity, etc. Preferably, such an inspection can be performed prior to entry into a process chamber as well as exit from the process chamber, thereby determining real time pre- and post-processing conditions of the substrate.

Other functions routinely performed in conventional processing systems and inspection systems include calibration of robots and the inspection equipment. Current methods of calibration negatively impact throughput because the system must be halted and opened in order to perform the calibration. A preferred processing system would allow for an integrated, or embedded, device capable of performing these various tasks in an integrated location and on-the-fly. Thus, the processing system could be further integrated and throughput can be increased. In addition, it would be preferable for such an integrated arrangement to be capable of monitoring robot behavior. Robot behavior of interest includes acceleration, speed, repeatability, stability, etc. A system adapted to monitor such robot characteristics would provide an apparatus and method to ensure consistent robot behavior regardless of the particular system in which the robot is implemented. Additionally, it would be preferable for such an integrated device to determine the presence of contamination on the robot blade which supports substrates during transfer. The presence of such contamination indicates that the backsides of substrates are being scratched during a substrate handling step. Heretofore, however, no such devices or methods has been known.

The inventors have discovered that the inspection device described herein can be adapted to perform numerous other inventive uses needed in processing systems such as those just described, e.g., the determination of selected substrate characteristics including reflectivity, substrate type, discontinuity, orientation and centerfinding, as well as performing calibration of robots and the inspection equipment and monitoring robot behavior. The following discussion provides various embodiments for the present invention but is not intended to be exclusive, as those skilled in the art will readily recognize other possible embodiments.

In one embodiment, the invention determines the substrate type. As noted above, the pattern of substrates provides a unique signature. Accordingly, the invention may be used to recognize substrates based on their pattern by scanning the substrate in the manner described above and transmitting the received signal to the EPI 86 for processing. The scanned pattern is then compared to stored signatures to determine the substrate type. Such an application provides the ability to detect a substrate that may have been misrouted through the system. For example, the OSA could detect and reject a substrate with photoresist which have been routed to a physical vapor deposition (PVD) chamber, thereby preventing potential damage to a process chamber and the substrate. In addition, recognition of the substrate pattern can be used to automatically change the process recipe according to the substrate type.

Further, the invention can be used to determine process uniformity, smoothness and substrate damage or defects, such as discontinuity (structural defects of the substrate due to thermal migration, for example, which may lead to portions of the substrate breaking off). In operation, the OSA and EPI 86 can be employed to generate a map of the substrate topology. The map can then be analyzed for texture characteristics such as planarity and uniformity. In addition, any substrate damage or defect, such as chips or fractures may be detected and mapped. Analysis can be enhanced by use of a color CCD detector.

Another substrate characteristic which may be determined, is the reflectivity of the substrate. Information regarding reflectivity can be used to determine whether certain process conditions have been successfully achieved, such as the endpoint of an etch process. Because the endpoint information is available in near real-time, i.e., substantially contemporaneously with the end of the process, and proximate the processing chamber, an under-processed substrate may be immediately returned for additional processing. Conventionally, substrates are taken to a remote location for endpoint examination. A subsequent determination that a substrate is under-processed typically results in the substrate being discarded because the time involved in returning the substrate for additional processing is cost prohibitive.

In another embodiment, the invention provides for Optical Character Recognition (OCR). OCR refers to the detection and processing of alphanumeric characters through video imaging. Substrates are often identified by characters which are typically inscribed on the substrate surface. The transmitter unit 56 and the receiver unit 58 of the present invention provide an apparatus capable of illuminating and detecting the characters and then directing a signal to the EPI 86 for processing. In operation, a substrate is scanned in the manner described above. During the scan the signal 54 will strike the characters on the substrate and be reflected according to the geometry of the characters. As with signal reflection by patterns, described above with reference to FIG. 6, the reflection is unique to the particular arrangement and configuration of the characters. Thus, the resulting signal can be compared to stored data representing previously scanned characters.

In another embodiment, the invention is used to determine a substrate's orientation and center. Orientation and center-finding are necessary to ensure proper positioning of the substrate in a chamber for particular processes. For example, etching involves the use of a mask to cover certain portions of the substrate surface. In order to position the mask on the appropriate portions of the substrate the orientation of the substrate must first be determined. The patterned surface of a properly oriented substrate on the blade provides a unique signature (as described above with reference to FIG. 6) which can be stored in a computer system such as the EPI 86. Thus, the present invention can be used to verify the signature. As a substrate is moved into the optical path 61 of receiver unit 58, the receiver unit 58 determines whether the signature is correct. If the signature is verified the conventional orientation task can be bypassed, thereby increasing throughput.

Substrate center-finding currently employs the use of one or more sensors to determine the center of a substrate. Use of the present invention enables substrate center-finding capability, thereby eliminating the need for additional sensors. Additionally, the components of the invention may be located outside of the vacuum environment of a processing system, thereby eliminating outgassing problems associated with conventional arrangements. During operation of the invention, a substrate is illuminated and scanned by the OSA (i.e., the transmitter unit 56 and the receiver unit 58) during the retraction, extension, and/or rotation of the blade. Thus, the diameter and, therefore, the center, of the substrate can be determined by the EPI 86. For example, as a substrate is moved into the path of the signal 54, the leading edge of a substrate is detected due to reflected light. Once the substrate passes through and beyond the signal 54, the receiver unit 58 ceases to detect a signal. The time between initial detection of a signal 54 and ceasing detection is recorded. For a known robot speed, the recorded time may be used to calculate the diameter of the substrate. If the substrate is determined not to be centered relative to a calibrated value, an adjustment is made to the destination coordinate of the robot 50 to correct the offset. It is understood that the particular method of calculating the substrate center is not limiting of the invention and people skilled in the art will recognize other possibilities. For example, in another embodiment, detection of the leading and lagging edges of a substrate, as described above, may be associated with the encoder value of the robot 50 at the time of detection. The encoder values can then be compared to calibrated values for substrates of the same diameter to determine any offset that must be accommodated.

In another embodiment, a substrate's orientation and center can be found while the substrate is positioned in a chamber, such as a cool down chamber, a degas chamber, or any other chamber of a processing system such as the one shown in FIG. 5. Center finding and orientation can be simultaneously done by positioning the substrate in the field of view of the receiver unit 58. The receiver unit 58 may be mounted in a view port of the chamber or in any other position wherein the receiver unit 58 can capture a substantial portion of the substrate in its field of view. In this manner, the chamber acts both as an area for analysis of the substrate as well as performing a processing function such as cooling or degassing. As a result, analysis can proceed without affecting the throughput of the processing system. The transmitter unit 56, rather than providing line-illumination as in the foregoing embodiments, is adapted to provide annular illumination about the perimeter of the substrate. Thus, the transmitter unit 56 may be a light-ring taking the form of a fiber optic-based light-ring, such as those commercially available from Fostee of Auburn, N.Y., and especially configured for machine vision and microscopy application. In one embodiment, the transmitter unit 56 is disposed at an upper end of the chamber opposite the substrate being examined. Thus, the side of the substrate facing the receiver unit 58 may be illuminated by the transmitter unit 56.

During operation, the substrate is positioned against a uniform background in the chamber. The transmitter unit 56 then illuminates the surface of the substrate and the uniform background. The illumination provides an image which is captured by the receiver unit 58. The image is then transmitted to the EPI 86 for processing. Analysis of the image by the EPI 86 is accomplished by identifying a contrast in optical density. A change in contrast can be identified by comparing the optical density of one area of the image to optical density of another area of the image. Because the substrate is positioned against a uniform background, analysis of the image taken by the receiver unit 58 will indicate a marked density contrast between the substrate and the uniform background. Thus, by analyzing contrast changes along the line or several lines of pixels the dimension and shape of the substrate can be determined. In addition, analysis of the entire image provided by the receiver unit 58 will map the substrate perimeter indicating the position of an orientation notch. In this manner, the center and the orientation of the substrate can be found simultaneously.

"Optical density contrast" refers to the change in contrast of the image received by the ESI 86 due to illumination of varying surfaces. Different surfaces (in the case the substrate and the background surface) produce different spectral results when illuminated, as described above with regard to spectral signatures. Such spectral variations can be analyzed by the EPI 86 to determine the dimensions of the substrate being illuminated.

In another embodiment wherein the transmitter unit 56 is a light-ring, the transmitter unit 56 may be placed to illuminate the back side of the substrate. Accordingly, the transmitter unit 56 is sized to have an inner diameter slightly less than the diameter of the substrate and the outer diameter slightly greater than the diameter of the substrate. As a result, the illuminating radiation of the transmitter unit 56 is provided to a perimeter portion of the back side of the wafer. While the substrate blocks a portion of the illuminating radiation from the receiver unit 58, a portion of the radiation outside the diameter of the substrate is visible to the receiver unit 58, thereby enhancing optical density contrast at the substrate edge. The resulting image provides a relatively darker area corresponding to the area occupied by the substrate.

For contrast analysis, the receiver unit 58 is preferably a two-dimensional CCD pixel array camera having lateral and vertical fields of view that span multiple pixels. In this manner, the acquired images provide multiple pixel rows and columns for quantification of a substrate's dimensions.

A contrast analysis, as described herein, can be implemented using well known machine vision techniques and commercially available systems for executing the same. For, example, machine vision systems capable of implementing contrast analysis techniques are available from Cognex Corporation of Matick, Mass. An example of a suitable machine vision system is the Cognex MVS 8000 series system, which includes a set of PC-based machine vision hardware and software tools. With such a system, the images can be analyzed on a pixel by pixel basis to evaluate optical density differences.

Accordingly, the invention provides an apparatus and method for generating realtime information about selected characteristics of a substrate. Substrate inspection is preferably performed before and after processing. A preferred operation of the invention may be understood with reference to FIG. 5. Upon transfer of a substrate from the transfer chamber 110 into a process chamber 114 or service chamber 116 by the robot 113, the invention preferably operates to scan the substrate in the manner described above. The result of the scan then produces information regarding substrate type, orientation, centerfinding, discontinuity, specular signature and presence of particles. Following processing, these same characteristics may be determined during the retraction of the substrate from the processing or service chamber. Additionally, a determination may be made regarding the process results. For example, the reflected signal from the substrate scan may be used to generate information on process uniformity and the process endpoint in the manner described above.

Thus, the invention provides real or near real-time pre- and post-processing information regarding characteristics of a substrate. Because the information is real-time an immediate cost efficient decision can be made about how to handle the substrate. Further, because each substrate may be inspected, as opposed to selected substrates from a batch, the information can be used to rectify identified problems with minimal damage to substrates and the processing environment.

In addition to inspecting a substrate, the invention is also adapted for calibration and health monitoring. In one embodiment, the invention may be used to calibrate the detection devices. Because the illumination and detection optics of the invention will not be uniform, the operation must be normalized. Normalization will be accomplished in the following way. When the OSA (the transmitter unit 56 and the receiver unit 58) is first installed, a substrate will be placed upside down on a robot blade. The robot blade will then move the substrate under the receiver unit 58. During the rotation of the blade both peak-to-peak and root-mean-square (RMS) measurements are made for each element of the detector 82. A comparison is then made between the average reading of each detector element to determine the correction factors necessary to normalize the system. Subsequently, the substrate is removed and the solid portion of the robot blade (i.e., excluding holes and edges) is then scanned in a similar fashion. The peak-to-peak and average for each detector element is then compared to the normalized correction factors to determine the blade correction factors. With the blade normalization factors in place, the blade can act as a resident calibration reference. Thus, the OSA can monitor the empty blade during normal operation to determine if the optics 62, 80 are functioning properly. If the optics 62, 80 are contaminated, or a detector element of the detector 82 degrades, it will be detected by the foregoing background test.

Additionally, contamination disposed on the surface of the blade 48 is also detected by the test described in the foregoing embodiment. Contamination on the blade 48 indicates that the backsides of substrates are being scratched at some point during the handling of the substrate. Thus, if contamination is detected on the blade, the system can be halted for inspection, thereby preventing further contamination to the processing environment.

In another embodiment, the OSA facilitates robot calibration. The processing system robots, such as the transfer chamber robot 50, periodically require calibration in order to ensure proper orientation and alignment. Because the OSA is mounted at a fixed location on a processing system, the OSA can provide a point of reference for the transfer chamber robot calibration. Once the blade normalization factors have been determined, as described above, the blade features can be detected to verify the robot position and proportional, integral and differential (PID) values. Sufficient variance between the detected position values and the calibrated position values stored by the EPI 86 indicates misalignment of the blade. The misalignment can be corrected by "homing" the robot according to the stored values.

The invention also enables monitoring of robot behavior. As the robot blade is rotated through the optical path 61 (shown in FIG.2) of the receiver unit 58, the blade edge nearest to the center of rotation will enter into the optical path 61 first. This edge will then enter the field-of-views (FOVs) of each detector element successively at a rate which is determined by the blade velocity. This allows the OSA to independently monitor the behavior of a robot including characteristics such as settling time, accelerations and stability can be measured/monitored. The collected data can be used to manually or automatically set the PID parameters of the robot.

Various other possible applications are not discussed here in detail. For example, the invention may be used to detect the presence of a substrate on a robot blade as well as determining whether the substrate is in a blade clamp used to secure the substrate during the movement of the blade. Those skilled in the art will recognize other applications contemplated by the present invention.

Thus, the invention facilitates the integration of numerous functions currently achieved by different components in a typical cluster tool. One or more single transmitter units 56 and receiver units 58 advantageously positioned, such as in a transfer chamber, can perform multiple functions including center-finding, orientation, particle inspection, damage inspection, robot behavior monitoring, etc. While such tasks are currently not preformed or are performed at various positions of the processing platform and require dedicated equipment, the invention provides a multi-purpose apparatus capable of achieving a higher level of system integration and reducing the system operating costs. By performing the substrate scanning methods described above on-the-fly, i.e., during necessary substrate transfer sequences, the impact to system throughput is minimized.

Which tasks are performable on a substrate is determined by a program product readable by the EPI 86. Preferably, the program product is software readable by the EPI and includes code to generate at least substrate positional information, substrate reflectivity information, specular information, substrate defect information, substrate damage information, particle contamination information for smooth and patterned substrates, particle contamination information for the robot blade, alphanumeric character information, robot behavior information, calibration information for the robot and the detection devices and any combination thereof. It is understood that the foregoing list is merely illustrative and other functions may be performed by the invention.

While the foregoing is directed to the preferred embodiment of the present invention, other and further embodiments of the invention may be devised without departing from the basic scope thereof, and the scope thereof is determined by the claims that follow.

What is claimed is:

1. A method for optical character recognition and particle detection, comprising:

transmitting an optical signal along a first path into a vacuum chamber of a multi-chamber semiconductor processing system including at least one substrate processing chamber;

moving a support member having a substrate disposed thereon from a first position to a second position in the vacuum chamber, wherein at least a portion of the substrate having alphanumeric characters inscribed thereon is moved through the first path, and wherein the support member is positionable in one or more chambers of the multi-chamber processing system;

detecting the presence of a reflected portion of the optical signal reflected by the alphanumeric character's geometry;

generating signal signature information representing the alphanumeric character's geometry;

comparing the signal signature information to a reference signal signature information; and determining an identity of the substrate based on a difference between the signal signature information and the reference signal signature information.

2. The method of claim 1, further comprising:

converting the reflected portion of the optical signal into data representing the alphanumeric characters; and comparing the data representing the alphanumeric characters with stored data.

3. The method of claim 1, further comprising:

detecting the presence of another reflected portion of the optical signal reflected by particles disposed on the substrate surface.

4. The method of claim 1, wherein detecting comprises receiving, at a receiver, at least some of the reflected portion of the optical signal representative of at least some of an alphanumeric character's geometry.

5. A method for optical character recognition on a substrate, comprising:

moving a substrate between a first position and a second position in a multi-chamber semiconductor processing system;

while moving the substrate, illuminating at least some portion of a substrate surface having at least one alphanumeric character inscribed thereon;

detecting a reflected signal from the substrate surface representing topographic data of the substrate surface;

generating signal signature information representing the topographic data;

comparing the signal signature information to a reference signal signature information; and determining the presence of the at least one alphanumeric character based on a difference between the signal signature information and the reference signal signature information.

6. The method of claim 5, wherein detecting comprises receiving, at a detector unit, a portion of the reflected signal.

7. The method of claim 5, wherein determining comprises generating at a process unit, data from the reflected signal representative of the at least one alphanumeric character.

8. A method for determining alphanumeric characters from a surface topography of a substrate, comprising:

supporting a substrate having alphanumeric characters inscribed on a surface of the substrate, moving the substrate from a first position to a second position within a vacuum chamber of a multi-chamber semiconductor processing system;

while moving the substrate, illuminating a portion of the substrate surface with a signal emitted from a source;

receiving a reflected portion of the signal from the illuminated portion of the substrate surface;

generating signal signature information representing the alphanumeric characters derived from the received reflected portion of the signal;

comparing the signal signature information to a reference signal signature information; and determining an identity of the substrate based on a difference between the signal signature information and the reference signal signature information.

9. The method of claim 8, further comprising, based on the comparing, determining that the topographical data corresponds to at least one of the alphanumeric characters.

10. The method of claim 8, wherein the refected portion of the signal represents at least a portion of the signal reflected from at least one of the alphanumeric characters.

11. The method of claim 7, further comprising determining a match between the generated alphanumeric character data from the reflected signal and stored alphanumeric character data match.

12. A method for optical character recognition, comprising:

transmitting an optical signal along a path into a vacuum chamber of a multi-chamber semiconductor processing system including at least one substrate processing chamber;

moving a support member having a substrate disposed thereon from a first position to a second position in the vacuum chamber, wherein at least a portion of the substrate having alphanumeric characters inscribed thereon is moved through the path;

illuminating the portion of the substrate having alphanumeric characters with the optical signal;

detecting a presence of a reflected portion of the optical signal reflected by a geometry of the alphanumeric characters;

generating signal signature information representing the alphanumeric character's geometry;

comparing the signal signature information to a reference signal signature information; and determining an identity of the substrate based on a difference between the signal signature information and the reference signal signature information.

13. The method of claim 12, wherein detecting the presence of the reflected portion of the optical signal comprises receiving, at a receiver, an electrical representation of the reflected portion of the optical signal representing at least one alphanumeric character.

14. The method of claim 12, further comprising detecting the presence of another reflected portion of the optical signal reflected by particles disposed on the substrate surface.

15. The method of claim 12, further comprising generating a signal indicative of the detected reflected potion of the optical signal.

16. The method of claim 15, further comprising directing the signal to a processing unit for signal processing.

17. The method of claim 16, comparing the signal to stored alphanumeric character data to determine a match.

18. The method of claim 12, further comprising generating, from the detected portion of the reflected optical signal, topographical data representing the alphanumeric characters.

19. The method of claim 18, further comprising comparing the topographical data to stored alphanumeric character data.

20. The method of claim 1, wherein the detecting step is performed in a front-end environment of a cluster tool comprising a transfer chamber connected to the front-end environment by at least one load lock chamber.

21. The method of claim 1, wherein the signal signature information and reference signal signature information are indicative of surface conditions of the substrate during a processing cycle.

22. The method of claim 1, wherein the determining step comprises determining a type of the substrate based on the difference between the signal signature information and the reference signal signature information.

23. The method of claim 1, wherein the determining step comprises determining an orientation of the substrate based on the difference between the signal signature information and the reference signal signature information.

* * * * *

UNITED STATES PATENT AND TRADEMARK OFFICE
CERTIFICATE OF CORRECTION

| | | |
|---|---|---|
| PATENT NO. | : 6,697,517 B1 | Page 1 of 1 |
| APPLICATION NO. | : 09/546644 | |
| DATED | : February 24, 2004 | |
| INVENTOR(S) | : Reginald Hunter | |

It is certified that error appears in the above-identified patent and that said Letters Patent is hereby corrected as shown below:

On the title page

Item [73], Assignee: Change Assignee's name from "Applied Magerials, Inc." to --Applied Materials, Inc.--

Column 1, Line 17: Change the heading "BACKGROUND OF THE RELATED INVENTION" TO --BACKGROUND OF THE RELATED ART--

Column 19, Claim 17, Line 17: Before "comparing", insert --further--

Signed and Sealed this
Twenty-eighth Day of June, 2011

David J. Kappos
*Director of the United States Patent and Trademark Office*